United States Patent
Zhao et al.

(10) Patent No.: US 11,318,172 B2
(45) Date of Patent: May 3, 2022

(54) **USE OF GENETICALLY ENGINEERED BACTERIUM OF ATTENUATED *SALMONELLA TYPHIMURIUM* IN FOR TREATING LIVER CANCER**

(71) Applicant: GUANGZHOU SINOGEN PHARMACEUTICAL CO., LTD, Guangzhou (CN)

(72) Inventors: Allan Zijian Zhao, Nanjing (CN); Sujin Zhou, Nanjing (CN); Yan Lin, Nanjing (CN); Zhenggang Zhao, Nanjing (CN); Fanghong Li, Nanjing (CN)

(73) Assignee: GUANGZHOU SINOGEN PHARMACEUTICAL CO., LTD, Guangzhou (CN)

( * ) Notice: Subject to any disclaimer, the term of this patent is extended or adjusted under 35 U.S.C. 154(b) by 0 days.

(21) Appl. No.: 17/067,636

(22) Filed: Oct. 9, 2020

(65) Prior Publication Data
US 2021/0077542 A1    Mar. 18, 2021

Related U.S. Application Data

(63) Continuation-in-part of application No. 15/755,537, filed as application No. PCT/CN2016/095629 on Aug. 17, 2016, now abandoned.

(30) Foreign Application Priority Data

Aug. 31, 2015   (CN) .......................... 201510546063.1

(51) Int. Cl.
| | | |
|---|---|---|
| *A61K 35/74* | (2015.01) | |
| *A61P 35/00* | (2006.01) | |
| *C12N 15/63* | (2006.01) | |
| *A61K 9/00* | (2006.01) | |

(52) U.S. Cl.
CPC ............ *A61K 35/74* (2013.01); *A61K 9/0019* (2013.01); *A61P 35/00* (2018.01); *C12N 15/63* (2013.01); *C12Y 404/01011* (2013.01)

(58) Field of Classification Search
None
See application file for complete search history.

(56) References Cited

FOREIGN PATENT DOCUMENTS

WO    WO-03063593 A1 *  8/2003  ............. A61K 45/06

OTHER PUBLICATIONS

Zhao et al (CN103961721, published Aug. 6, 2014; English translation).*

* cited by examiner

*Primary Examiner* — Brian Gangle
(74) *Attorney, Agent, or Firm* — Jun He Law Offices P.C.; James J. Zhu (57) ABSTRACT

Provided is use of a genetically engineered bacterium of attenuated *Salmonella typhimurium* for treating liver cancer. The bacterium is attenuated *Salmonella typhimurium* VNP20009 carrying a plasmid cloned with a methioninase gene. Also provided is a construction method of the bacterium.

5 Claims, 6 Drawing Sheets

PBS

VNP20009-V

VNP20009-M

USE OF GENETICALLY ENGINEERED BACTERIUM OF ATTENUATED *SALMONELLA TYPHIMURIUM* IN FOR TREATING LIVER CANCER

CROSS REFERENCE TO RELATED APPLICATIONS

This application is a continuation-in-part of U.S. patent application Ser. No. 15/755,537, which is the national phase of international application PCT/CN2016/095629, filed Aug. 17, 2016, which claims priority benefits from Chinese patent application no. 201510546063.1, filed Aug. 31, 2015, the disclosure of which is hereby incorporated herein by reference.

FIELD OF THE INVENTION

The present invention relates to the field of pharmaceutical technology, and in particular, to the use of a genetically engineering bacterium of attenuated *Salmonella typhimurium* for treating liver cancer.

BACKGROUND

Liver cancer is one of the most common malignancies in the world. The incidence of liver cancer in china is highest around the world and is the second most common cancer after lung cancer. The populations with liver cancer in china account for 45% of the world, and its mortality rate ranks third among malignant tumors. The treatment of liver cancer mainly includes surgery, radiotherapy and chemotherapy. Since liver cancer has poor sensitivity to radiotherapy, and treatment of conventional chemotherapy drugs (such as doxorubicin, fluorouracil, cisplatin) has serious toxic and side effects and cannot apparently alleviate the disease, surgical resection is still the main approach for the treatment of liver cancer. However, the onset of liver cancer is insidious without typical symptoms during the early period. The tumor cells grow rapidly, resulting in rapid progression and high degree of malignancy, so less than 30% of patients can receive surgical treatment. Even after surgery, the recurrence rate is also very high, so the prognosis of patients with liver cancer is very poor. According to relevant statistical data, the treatments fail for more than 95% of patients with liver cancer. At present, there is an enormous unmet clinical demand for the drugs to treat liver cancer, and it is urgent to develop new and effective therapeutic drugs.

*Salmonella* is a group of gram-negative, invasive intracellular facultative anaerobes that are parasitic in intestines of humans and animals. VNP20009 is an attenuated *Salmonella typhimurium* strain with deletion of msb B, pur I genes. It is genetically stable, susceptible to antibiotics. The msbB gene is necessary for the lipid acylation to endotoxin, and its deletion prevents the lipid A terminal from being acylated to reduce toxicity. The pur I gene is involved in purine metabolism, and when deletion, the bacterial reproduction needs exogenous adenine. VNP20009 also reduces the tumor necrosis factor (TNF) induced by itself, resulting in reduced inflammatory response. Therefore, the low pathogenicity of VNP20009 enhances its safety for clinical treatment. VNP20009 has been widely used in cancer studies. It can act on a variety of mouse solid tumor models, including melanoma, lung cancer, colon cancer, breast cancer, kidney cancer. One of the major advantages of VNP20009 as a tumor gene therapy vector is that it can aggregate at the tumor in a highly targeted manner. Researchers have found that, in a variety of mouse models of solid tumors, the amount of VNP20009 in the tumors is higher than that in the major organs such as liver by 200-1000 times. VNP20009 can aggregate and reproduce in priority in the hypoxic necrosis zone of tumor tissues. And within the same period of time, the passage number of bacteria in the tumor tissues is significantly higher than that in normal tissues, making attenuated *Salmonella* as a new anti-tumor agent and a vector of tumor targeted therapy. The possible mechanism of slowed tumor growth caused by *Salmonella*: the nutrients required for tumor growth are consumed by bacteria, and the enzymes produced by bacteria such as asparaginase, can deplete the essential amino acids required for the growth of tumors; the local toxins or tumor necrosis factor α secreted by bacteria to the extracellular microenvironment can affect tumor angiogenesis; in addition, non-specific inflammatory responses at the site of bacterial growth can potentially activate anti-tumor T cells.

Tumor cells need adequate nutrition to maintain its high proliferation rate. In addition to carbohydrates, the needs for methionine (Methionine, Met), glutamine, arginine are particularly great. Previous studies have shown that Met-dependency is a common feature of most tumor cells, such as breast cancer, liver cancer, lung cancer, colon cancer, kidney cancer, bladder cancer, melanoma, glioma, etc., while Met dependency does not exist in normal cells. In vivo and in vitro experiments have successively confirmed that dietary intervention with methionine deficiency can delay the proliferation of tumor cells. However, long-term deficiency of Met can cause malnutrition, metabolic disorders, and aggravate tumor growth due to a long-term DNA hypomethylation. Thus, by specifically degrading Met through L-methioninase, the methionine in the body is reduced, which can be more effective in inhibiting tumor growth or degrading them. Experiments in animal models have shown that intraperitoneal injection of methioninase can inhibit the growth of Yoshida sarcoma and lung tumor in nude mice. In clinical trials, four patients with breast cancer, lung cancer, renal cell carcinoma and lymphoma respectively received methioninase injection once every 24 h. Methioninase could significantly reduce methionine content in plasma. However, since methionine is not expressed in mammal itself, the exogenous administration may have some side effects, often causing the body's immune response.

SUMMARY

The object of the invention is to provide use of genetically engineered bacterium for treating liver cancer.

In one aspect, the present disclosure provides a method for treating liver cancer in a human subject in need thereof, the method comprising administering a therapeutically effective amount of a genetically engineered strain VNP20009-M to the human subject. In some embodiments, the genetically engineered strain VNP20009-M is an attenuated *Salmonella typhimurium* VNP20009 comprising an L-methioninase gene. In some embodiments, the therapeutically effective amount is a dose of about $5 \times 10^7$ CFU/m$^2$ body surface area (BSA) to about $3 \times 10^8$ CFU/m$^2$ BSA.

In some embodiment, the genetically engineered bacterium VNP20009-M is an attenuated *Salmonella typhimurium* VNP20009 which comprises a vector comprising the L-methioninase gene.

In some embodiment, the vector is a pSVSPORT plasmid, a pTrc99A plasmid, a pcDNA3.1 plasmid, a pBR322 plasmid or a pET23a plasmid.

In some embodiment, the genetically engineered strain VNP20009-M is constructed according to the following method: inserting the L-methioninase gene into the vector to obtain an L-methioninase expression plasmid; electro-transforming the L-methioninase expression plasmid to attenuated *Salmonella typhimurium* VNP20009; and obtaining the VNP20009-M.

In some embodiment, the electro-transformation condition is as follows: voltage 2400V, resistance 400Ω, capacitance 25 μF, discharge time 4 ms.

In some embodiment, the genetically engineered strain VNP20009-M is administered to the human subject via intravenous injection.

In some embodiment, the genetically engineered strain VNP20009-M is administered to the human subject once every ten days, once every week or twice every week.

The present invention can achieve the following beneficial effects. Compared with prior art, the invention for treating liver cancer is a kind of novel biological medicine, which is safe and non-toxic, and has anti-tumor activity. By using attenuated *Salmonella typhimurium* VNP20009 as a vector to highly express methioninase through gene recombination, the biological medicine has strong anti-tumor activity. The manufacturing process of the biological medicine is simple and easy to operate, with good application prospect.

DETAILED DESCRIPTION

In the Summary above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Definitions

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

As used herein, the term "CFU" or "cfu" or "colony-forming unit" means a unit used to estimate the number of viable bacteria cells in a sample. Viable means the ability to multiply via binary fission under the controlled condition. CFU can be measured by culturing the bacteria under the controlled condition and counting the number of colonies grown from single bacteria cells.

As used herein, an "effective amount" or "therapeutically effective amount" means the amount of agent that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount sufficient to reduce or eliminate a symptom of a disease. In another embodiment, a therapeutically effective amount is an amount sufficient to overcome the disease itself.

As used herein, the term "subject" refers to a human or any non-human animal (e.g., mouse, rat, rabbit, dog, cat, cattle, swine, sheep, horse or primate). A human includes pre and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, the term "vector" means a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Method of Treating Liver Cancer

With the development of the genetic engineering and targeting technology of bacteria and virus, there are more and more studies on the bacterial treatment of cancers since the middle of 1990s. Researchers have found that typhoid *Salmonella* can be used as a good gene vector to effectively kill tumor cells in the body of mice in a targeted manner. *Salmonella* is a group of gram-negative, invasive intracellular facultative anaerobes that are parasitic in intestines of humans and animals. VNP20009 is an attenuated *Salmonella typhimurium* strain with deletion of msb B and pur I genes. It is genetically stable and susceptible to antibiotics. The msb B gene is necessary for the lipid acylation to form endotoxin, and its deletion prevents the lipid A terminal from being acylated and reduces toxicity. The pur I gene is involved in purine metabolism. Bacteria of pur I deletion needs exogenous adenine to reproduce. VNP20009 also reduces tumor necrosis factor (TNF) induced by typhoid *Salmonella*, resulting in reduced inflammatory response. Therefore, the low pathogenicity of VNP20009 enhances its safety for clinical treatment. VNP20009 has been widely used in cancer studies. It can act on a variety of mouse solid tumor models, including melanoma, lung cancer, colon cancer, breast cancer, kidney cancer. One of the major advantages of VNP20009 as a tumor gene therapy vector is that it can aggregate at the tumor sites in a highly targeted manner. Researchers have found in a variety of mouse models of solid tumors that the amount of VNP20009 in the tumors is higher than that in the major organs such as liver by 200-1000 times. VNP20009 can aggregate and reproduce in priority in the hypoxic necrosis zone of tumor tissues. And within the same period of time, the passage number of bacteria in the tumor tissues is significantly higher than that in normal tissues, making attenuated *Salmonella* as a new anti-tumor agent and a vector of tumor targeted therapy. The possible mechanism of slowed tumor growth caused by *Salmonella* includes the nutrients required for tumor growth are consumed by the bacteria, and the enzymes produced by the bacteria such as asparaginase, can deplete the essential amino acids required for tumor growth. Furthermore, the local toxins or tumor necrosis factor α secreted by the bacteria to the extracellular microenvironment can affect tumor angiogenesis. In addition, non-specific inflammatory responses at the site of bacterial growth can potentially activate anti-tumor T cells. However, the inhibitory effect of VNP20009 on tumor metastasis has not been found yet.

The present invention is based on a surprising finding that a genetically engineered strain VNP20009-M can effectively prevent and treat liver cancer. Therefore, one aspect of the present disclosure provides a method for treating liver cancer in a subject. In one embodiment, the method comprises administering a therapeutically effective amount of a genetically engineered strain VNP20009-M to the subject.

In one embodiment, the genetically engineered strain VNP20009-M is an attenuated *Salmonella typhimurium* VNP20009 cloned with an L-methioninase gene. In certain embodiments, the genetically engineered bacterium VNP20009-M is an attenuated *Salmonella typhimurium* VNP20009 which comprises a plasmid cloned with an L-methioninase gene.

In certain embodiments, the genetically engineered strain VNP20009-M as provided herein may be administered at a therapeutically effective dosage of about $3 \times 10^7$ CFU/m$^2$ body surface area (BSA) to about $3 \times 10^8$ CFU/m$^2$ BSA. In certain of these embodiments, the genetically engineered strain VNP20009-M is administered at a dosage of about $5 \times 10^7$ CFU/m$^2$ BSA to about $3 \times 10^8$ CFU/m$^2$ BSA, and in certain of these embodiments the dosage is about $5 \times 10^7$ CFU/m$^2$ BSA to about $1 \times 10^8$ CFU/m$^2$ BSA, $5 \times 10^7$ CFU/m$^2$ BSA to about $2 \times 10^8$ CFU/m$^2$ BSA, about $3 \times 10^7$ CFU/m$^2$ BSA to about $2 \times 10^8$ CFU/m$^2$ BSA, about $5.5 \times 10^7$ CFU/m$^2$ BSA to about $1.6 \times 10^8$ CFU/m$^2$ BSA, about $3 \times 10^7$ CFU/m$^2$ BSA, about $5 \times 10^7$ CFU/m$^2$ BSA, about $1 \times 10^8$ CFU/m$^2$ BSA, about $1.5 \times 10^8$ CFU/m$^2$ BSA, about $2 \times 10^8$ CFU/m$^2$ BSA or about $3 \times 10^8$ CFU/m$^2$ BSA.

The method to calculate body surface area of a human subject is known in the art, including without limitation, Du Bois formula (BSA=$0.007184 \times W^{0.425} \times H^{0.725}$), Mosteller formula (BSA=$0.016667 \times W^{0.5} \times H^{0.5}$), Haycock formula (BSA=$0.024265 \times W^{0.5378} \times H^{0.3964}$), whereas W means weight of a human subject, H means the height of the human subject.

In certain embodiments, the genetically engineered strain VNP20009-M as provided herein may be administered at a therapeutically effective dosage of about $1 \times 10^6$ CFU/kg body weight to about $1 \times 10^7$ CFU/kg body weight. In certain of these embodiments, the genetically engineered strain VNP20009-M is administered at a dosage of about $1 \times 10^6$ CFU/kg body weight to about $8 \times 10^6$ CFU/kg body weight, and in certain of these embodiments the dosage is about $1 \times 10^6$ CFU/kg body weight to about $5 \times 10^6$ CFU/kg body weight, $1.5 \times 10^6$ CFU/kg body weight to about $4.5 \times 10^6$ CFU/kg body weight, $1.5 \times 10^6$ CFU/kg body weight to about $7 \times 10^6$ CFU/kg body weight, about $1 \times 10^6$ CFU/kg body weight, about $1.5 \times 10^6$ CFU/kg body weight, about $4.5 \times 10^6$ CFU/kg body weight, about $7 \times 10^6$ CFU/kg body weight or about $1 \times 10^7$ CFU/kg body weight.

In certain embodiments, the administration dosage may change over the course of treatment. For example, in certain embodiments the initial administration dosage may be lower than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

In certain embodiments, the routes of administration for treating cancers include, but not limited to, oral administration, topical administration, injection administration (including but not limited to intravenous, peritoneal, subcutaneous, intramuscular, intratumoral administration), etc.

The present invention can be better understood from the following examples. However, it will be readily understood by those skilled in the art that the embodiments described are intended to be illustrative of the invention, not and should not be construed as limiting the invention as set forth in the claims.

Example 1

The following example illustrates the construction of genetic engineering bacterium (1) Construction of a plasmid expressing the L-methioninase gene The L-methioninase (GenBank: L43133.1) gene is synthesized and subcloned to pUC57 plasmid (Genscript), then subcloned to pSVSPORT plasmid (invitrogen) through the Kpn I and Hind III restriction sites, to get the pSVSPORT-L-methioninase expression plasmid. The specific procedure is as follows:

The pSVSPORT plasmid was digested with Kpn I and Hind III, with the digestion system: 2 μg of plasmid DNA, 3 mL of 10× buffer, 1.5 μL of Kpn I enzyme, 1.5 μL of Hind III enzyme, added with ddH2O to 30 μL, incubate warm bath for 3h at 37° C., then the digestion system was separated by 1% agarose gel electrophoresis in 1% agarose gel, to cut out DNA bands at a with the size of 4.1 kb, then DNA was purified by gel recovery and purification kit.

DNA fragments of L-methioninase coding region were obtained by gene synthesis and subcloned to pUC57 plasmid (Genscript), digested with Kpn I and Hind III, with the digestion system: 3 μg of plasmid DNA, 3 mL of 10× buffer, 1.5 μL of Kpn I enzyme, 1.5 μL of Hind III enzyme, added with ddH2O to 30 μL, warm bath for 3 h at 37° C., then the digestion system was separated by 1% agarose gel electrophoresis in 1% agarose gel, to cut out DNA bands at a with the size of 1.2 kb, then DNA was purified by gel recovery and purification kit.

The pSVSPORT (Kpn I/Hind III) and DNA fragment of the L-methioninase coding region (Kpn I/Hind III) were ligated. The ligation reaction condition: 2 mL of vector, 6 L of inserted fragment, 1 μL of T4 DNA ligase, water bath for 16 h at 16° C.

The ligation product was transformed into competent cells of *E. coli* DH5a (Takara). One tube of 50 mL DH5a competent cells was placed on the ice until thawing molten, then 5 μL of above ligation product was added, mixed well by flicking, incubated on ice for 30 min; after heat shock 60 s at 42° C., placed on ice for 2 min; then 500 μL of non-resistant LB liquid medium was added and incubated at 37° C. for 1 h with shaking, then spread on ampicillin resistant LB medium plate and cultured overnight.

Figure 1:
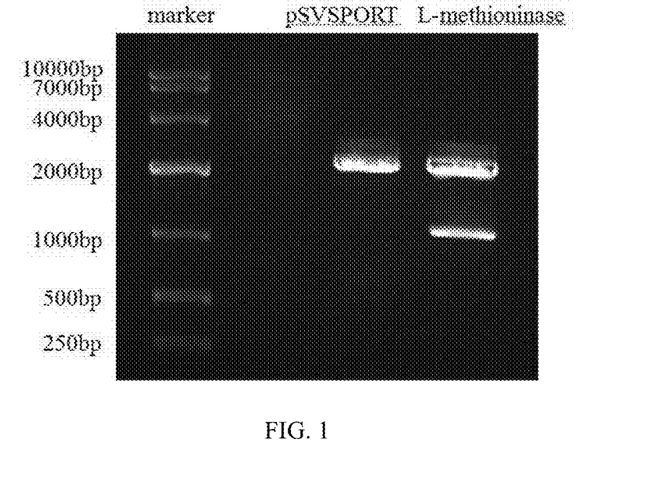
FIG. 1 shows the 1% agarose gel electrophoresis of plasmid pSVSPORT-L-methioninase digestion assay.

When clones grew, single clone was inoculated to 3 mL of ampicillin-containing LB medium, incubated at 37° C. for 16 h. The plasmid DNA was extracted and identified by Kpn I and Hind III digestion. Two DNA bands at the size of 4.1 kb, 1.2 kb were obtained in the positive clones, as shown in FIG. 1. The sequence of the positive clones was further confirmed by sequencing.

(2) Construction of plasmid-bearing VNP20009 strain and VNP20009 strain bearing a plasmid cloned with L-methioninase gene The pSVSPORT and pSVSPORT-L-methioninase expression plasmids are electro-transformed to VNP20009 strain (YS1646, ATCC No. 202165) respectively, and named as VNP20009-V and VNP20009-M, respectively. The specific construction process is as follows:

The competent bacteria VNP20009 was placed on ice, after melted, transferred to a pre-cooled electric rotating-cup and 2 mL of the plasmid was added, mixed well by flicking, incubated on ice for 30 min; after heat shock 60s at 42° C., placed on ice for 1 min. The electric rotating-cup was placed into an electroporator, and the condition was set to voltage 2400V, resistance 400Ω, capacitance 25 μF, discharge time 4 ms. After the electric shock, 1 mL SOC medium was added and mixed well gently, incubated at 37° C. for 1 h with shaking. After the bacterial precipitation was blown by a pipette and uniformly spread on an ampicillin-resistant LB-O medium plate, then incubated 16 h at 37° C. incubator. After the VNP20009-V and VNP20009-M were cultured with LB-O, the plasmids were extracted and identified by restriction enzyme digestion.

Figure 2:
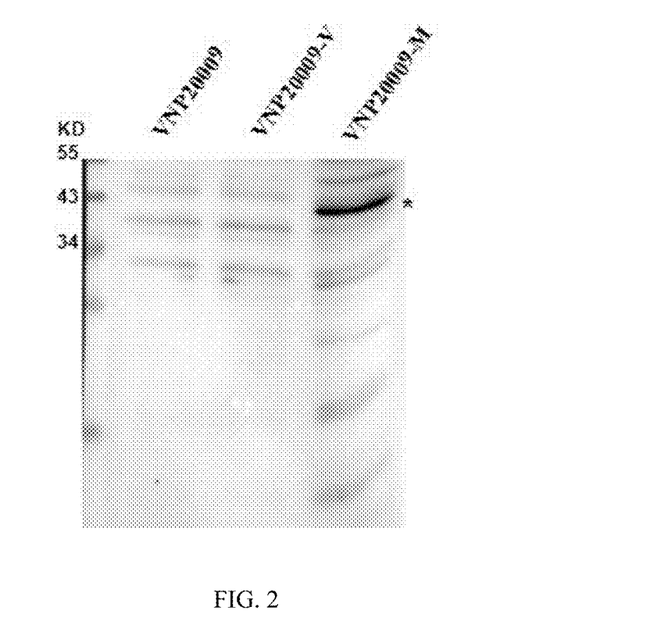
FIG. 2 shows the Western blot analysis of methioninase expression.

The protein was extracted from $1 \times 10^8$ *Salmonella* and separate by 10% SDS-PAGE electrophoresis, transferred to PVDF membrane under constant voltage, after blocked 1 h with BSA at room temperature, rinsed 3×5 min with TBST, added with the rabbit anti-L-methioninase antibody (1:1000) overnight at 4° C., rinsed with TBST 3 times, 5 min each time, then HRP labeled anti-rabbit secondary antibody (1:10000) was added, incubated at room temperature for 1 h, rinsed with TBST 3 times, 5 min each time, developed using the enhanced chemiluminescent (ECL). The results are shown in FIG. 2. Specific bands were found at about 43 kD molecular weight, indicating that the expression of L-methioninase significantly increased in VNP20009-M compared with that in VNP20009 and VNP20009-V.

Figure 3:
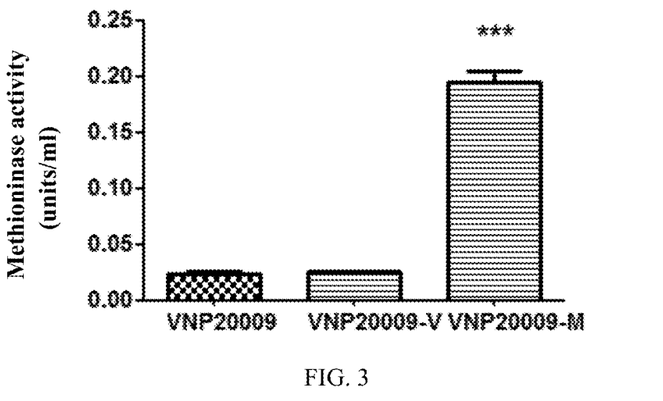
FIG. 3 shows the detection of methioninase activity in *Salmonella*.

L-methionine and pyridoxal were mixed with VNP20009-V and VNP20009-M strains respectively, and incubated at 37° C. for 10 min. After terminated by 50% trichloroacetic acid, the mixed solution was centrifuged to get the supernatant, then well mixed with 3-methyl-2 MBTH; after incubated at 50° C. for 30 min, the absorbance at 320 nm was determined. The amount of enzyme that catalyzes to covert α-ketobutyric acid was defined as one unit of enzyme activity. The results are shown in FIG. 3. The methioninase activity of *Salmonella* VNP20009-M was 10 times higher than that of VNP20009-V.

Example 2

The following example illustrates the anti-tumor effect of VNP20009-L-methioninase strain in mouse model of liver cancer 1. Highly metastatic HCC cell HCCLM3 is cultured in DMEM medium containing 10% fetal bovine serum. $2 \times 10^6$ cells are inoculated subcutaneously on the right armpit of nude mice. The tumor-bearing nude mice are randomized as: PBS control group, VNP20009-V group and VNP20009-M group.

Figure 4:
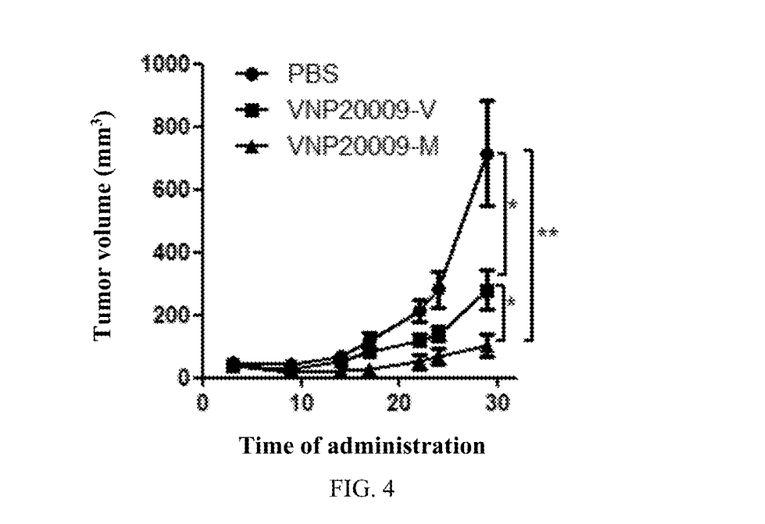
FIG. 4 shows the curve of tumor volume change after administration of *Salmonella*.
Figure 5:
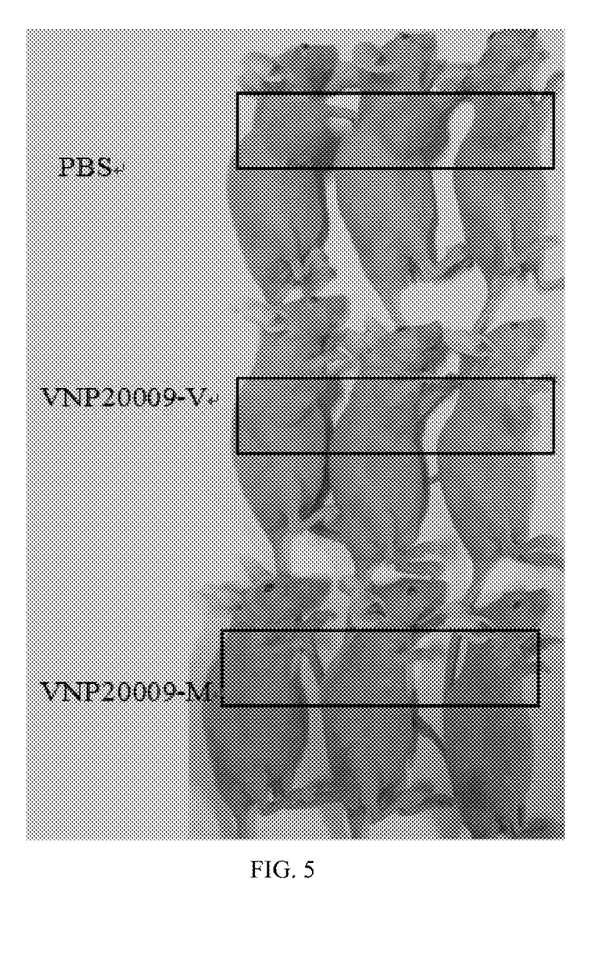
FIG. 5 shows the tumor size of mice anesthetized 4 weeks after administration of *Salmonella*. The black frame indicates the tumor.
Figure 6:
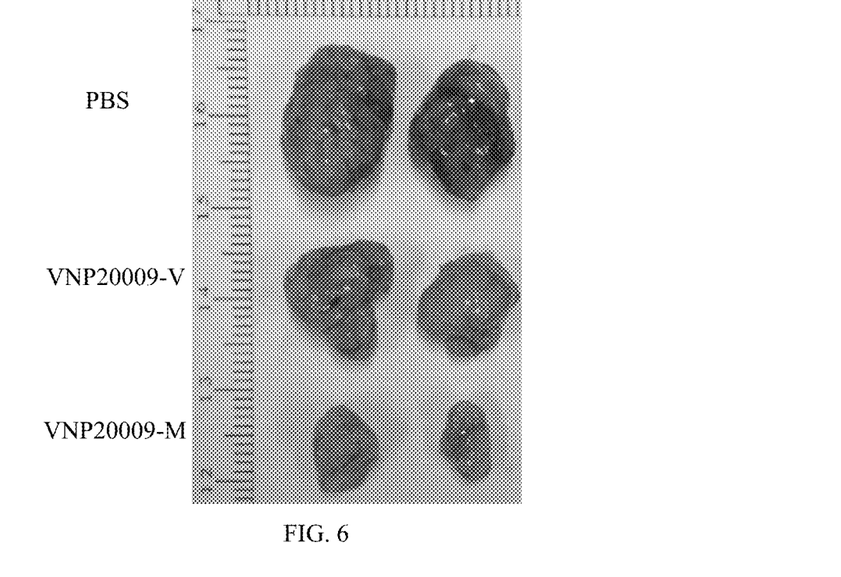
FIG. 6 shows the tumor size 4 weeks after administration of *Salmonella*.
Figure 7:
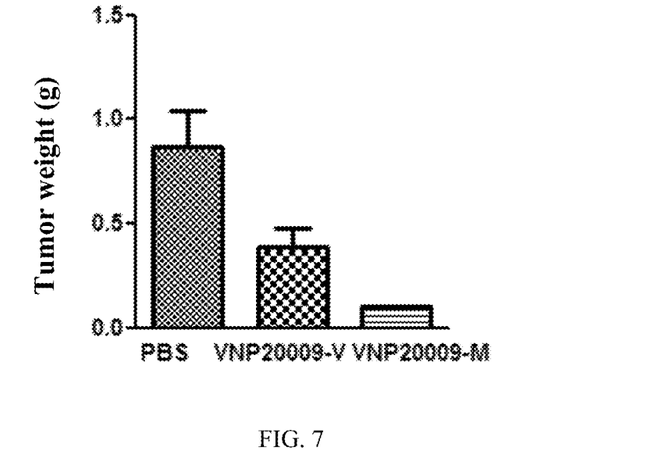
FIG. 7 shows the tumor weight 4 weeks after administration of *Salmonella*.

2. VNP20009-V and VNP20009-M are cultured with LB-O. When OD≈0.6, the cells are harvested and resuspended in PBS. On the third day after inoculation, mice are administered at a dose of $1 \times 10^4$ CFU/g (about $2 \times 10^5$ CFU/mouse) by tail vein injection while the control group are administered with the same volume of PBS. The mice are observed every 2-3 days after administration. The tumor size is measured by a vernier caliper (volume=0.52×length×width$^2$), and the tumor volume change curves of nude mice are plotted (FIG. 4). On the 30th day after administration, three mice are randomly selected from each group to anesthetize and photograph (FIG. 5). Two mice are randomly selected from the control group and test group separately. The tumors of nude mice are dissected, weighed and photographed (FIGS. 6, 7). The results are shown in FIGS. 4 and 5. After modeling, the tumors of the mice in the PBS and blank groups grow normally and increase quickly; while after administration of *Salmonella* VNP20009-M, the tumors are shrank or even completely disappear in some mice. The growth of tumors stops in most mice in the VNP20009-M group, and the tumor volume and weight (FIGS. 6 and 7) are about ½ of those in the VNP20009-V group and ⅕ of those in the PBS group. These results show that *Salmonella* VNP20009-M has a significant inhibitory effect on the liver tumor.

Figure 8:
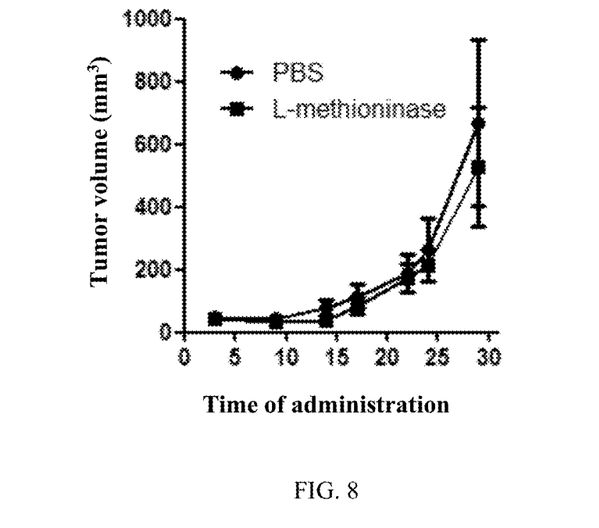
FIG. 8 shows the curve of tumor volume change after administration of L-methioninase.

3. The procedures are the same as those in 1. Tumor-bearing nude mice are divided into two groups and administered with PBS or L-methioninase at a dose of 100 ng/mouse respectively by intravenous injection. The tumor size is measured by a vernier caliper (volume=0.52×length×width$^2$) and the tumor volume change curves of nude mice are plotted. As shown in FIG. 8, there is no significant difference in the tumor size between two groups. The dose of L-methioninase at 1 ng/mouse is equivalent to that of L-methioninase contained in $2 \times 10^6$ CFU VNP20009-M. Thus, a 100-fold dose of L-methioninase has no significant anti-tumor effect. This indicates that, with the depletion or degradation of L-methioninase, a single administration does not function, while the sustained high expression of L-methioninase using VNP20009 as a carrier can make up this defect, showing a significant anti-tumor effect.

The invention has showed that genetic engineering bacterium has a significant inhibitory effect on HCC cells. The attenuated *Salmonella typhimurium* VNP20009 carrying a plasmid cloned with a L-methioninase gene can continuously express L-methioninase in the liver tumor tissues, which consumes a large amount of methionine and other nutrients, so that the tumor cells are lack of nutrition and grow slowly. Therefore, it can be used in the manufacture of medicaments for treating liver cancer. The plasmid is not limited to a pSVSPORT plasmid. The pTrc99A plasmid, pcDNA3.1 plasmid, pBR322 plasmid or pET23a plasmid and the above plasmids cloned with L-methioninase gene have similar effects.

Example 3

The following example illustrates the anti-tumor effect of VNP20009-L-methioninase strain in a human patient.

In March 2016, a 60-year-old man had a pain in his upper abdomen with no apparent cause. Abdominal ultrasonography revealed liver cirrhosis and hepatic masses. In May 2016, he underwent left liver resection, with pathology confirming hepatocellular carcinoma. The cut surface of the resected liver specimen showed two tumors, measuring 3 cm×2.5 cm and 2.2 cm×2.5 cm in size. Tumor thrombus located in the lymphatic vessel with no infiltration of nerves and the margin of the resection was negative. Thus, the patient did not take any herbs or other curative therapy after surgery. Unfortunately, follow-up dynamic contrast-enhanced Magnetic Resonance Imaging (MRI) showed that multiple lesions in right lobe of the liver which indicated cancer recurrence in October 2016.

Figure 9:
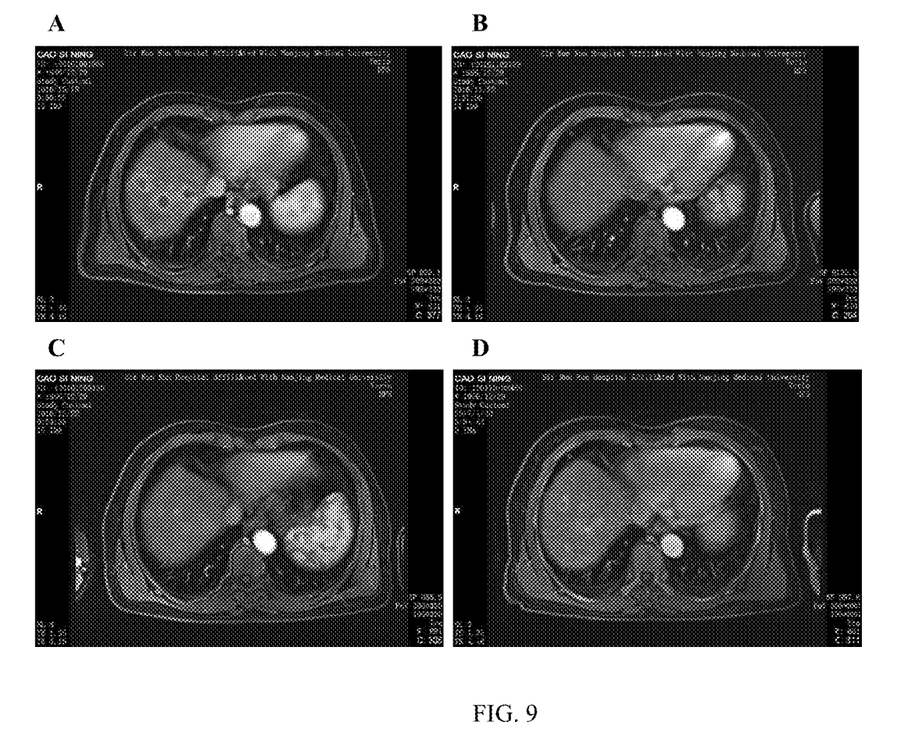
FIG. 9 shows the contrast-enhanced Magnetic Resonance Imaging (MRI) in the arterial phase in a patient treated with VNP20009-M. (A) Image at the start of VNP20009-M administration. (B, C, D) Images at 1, 2, 3 months after VNP20009-M administration, respectively.

The patient received attenuated *Salmonella Typhimurium* VNP20009-M via intravenous injection at the initial dose of $5.5 \times 10^7$ CFU/m$^2$ on Oct. 18, 2016. The patient received VNP20009-M once every week for up to three weeks and then twice every week for up to 3.5 months. Two months after initial administration, the dosage of VNP20009-M was increased to $1.65 \times 10^8$ CFU/m$^2$. The patient tolerated the therapy well with minimal toxicities, except for the onset of transient chills, fever and vomiting on the day of treatment. At the time of hospitalization, the patient was regularly followed-up with MRI and laboratory tests. A contrast-enhanced MRI of the liver obtained after one month of therapy showed a significant reduction of tumor-burden with a decrease in the number and size of the mass (FIG. 9). The significant curative effects maintained for 3 months. The patient achieved a partial response by Response Evaluation Criteria in Solid Tumors (RECIST), version 1.1.

Example 4

The following example illustrates the anti-tumor effect of VNP20009-L-methioninase strain in another human patient.

In August 2016, a 78-year-old woman complained of having nausea, vomiting, and diarrhea for four months. Abdominal ultrasonography revealed hepatic masses which were confirmed hepatocellular carcinoma using ultrasound-guided percutaneous needle biopsy. MRI revealed one huge These masses located at the top and right lobe of the liver, with a maximum size of 14 cm×7 cm. The patient underwent abdominal computed tomography (CT), which demonstrated lung metastases. The concentration of serum alpha-fetoprotein (AFP) exceeded 475 ng/ml (normal range: 0-7). All together, the patient was then diagnosed with stage IV HCC on the basis of the clinical presentation.

Figure 10:
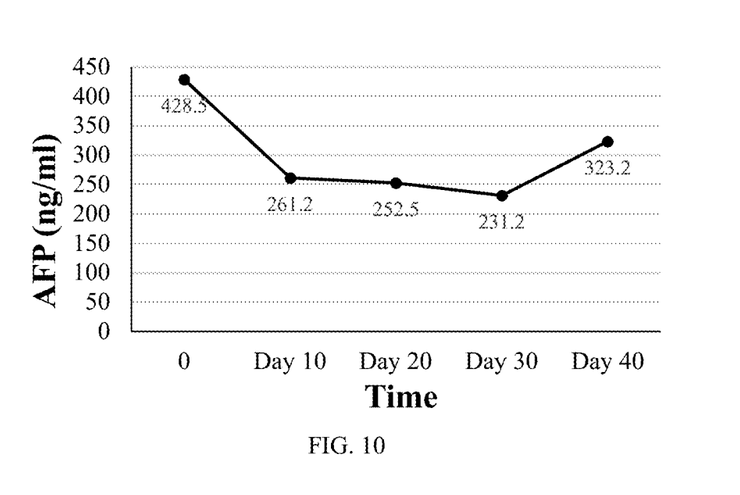
FIG. 10 shows the clinical course of serum alpha-fetoprotein (AFP) in a patient treated with VNP20009-M.

The patient received attenuated *Salmonella Typhimurium* VNP20009-M via intravenous injection at the initial dose of $5.7 \times 10^7$ cfu/m$^2$ on Sep. 14, 2016. The patient received VNP20009-M once every week for up to one month. The patient also tolerated the therapy well and had transient chills, fever and vomiting on the day of treatment. Ten days after initial treatments, the concentration of serum AFP dramatically declined to 261.2 ng/ml (FIG. 10) and had improvement in nausea and diarrhea. With the normalization of AFP level, suggesting lower tumor burden, her symptoms were gradually improved. However, because the patient didn't want to hospitalized out-of-town, she quitted the treatment. The AFP level quickly rebounded to 323.2 ng/ml at ten days after termination of treatment.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

The invention claimed is:

1. A method for treating liver cancer in a human subject in need thereof, the method comprising administering a therapeutically effective amount of a genetically engineered strain VNP20009-M to the human subject, wherein the genetically engineered strain VNP20009-M is an attenuated *Salmonella typhimurium* VNP20009 comprising an L-methioninase gene, wherein the therapeutically effective amount is a dose of about $5 \times 10^7$ CFU/m$^2$ body surface area (BSA) to about $3 \times 10^8$ CFU/m$^2$ BSA, and wherein the genetically engineered strain VNP20009-M is administered to the human subject once or twice every week.

2. The method according to claim 1, wherein the genetically engineered bacterium VNP20009-M is an attenuated *Salmonella typhimurium* VNP20009 which comprises a vector comprising the L-methioninase gene, wherein the vector is a pSVSPORT plasmid, a pTrc99A plasmid, a pcDNA3.1 plasmid, a pBR322 plasmid or a pET23a plasmid.

3. The method according to claim 2, wherein the genetically engineered strain VNP20009-M is constructed according to the following method: inserting the L-methioninase gene into the vector to obtain an L-methioninase expression plasmid; electro-transforming the L-methioninase expression plasmid to attenuated *Salmonella typhimurium* VNP20009; and obtaining the VNP20009-M.

4. The method according to claim 3, wherein the electro-transformation condition is as follows: voltage 2400V, resistance 400Ω, capacitance 25 μF, discharge time 4 ms.

5. The method according to claim 1, wherein the genetically engineered strain VNP20009-M is administered to the human subject via intravenous injection.

* * * * *